(12) United States Patent
Anna et al.

(10) Patent No.: US 11,963,993 B2
(45) Date of Patent: Apr. 23, 2024

(54) PROCESS FOR OBTAINING A TANNIN EXTRACT ISOLATED FROM GRAPES, TANNIN EXTRACT OBTAINED AND USES THEREOF

(71) Applicant: UNIVERSITAT DE LLEIDA, Lleida (ES)

(72) Inventors: Bacardit Dalmases Anna, Igualada (ES); Ollé Otero Luis, Igualada (ES); Sorolla Casellas Sílvia, Igualada (ES); Casas Solé Concepció, Igualada (ES)

(73) Assignee: Universitat de Lleida, Lleida (ES)

( * ) Notice: Subject to any disclaimer, the term of this patent is extended or adjusted under 35 U.S.C. 154(b) by 466 days.

(21) Appl. No.: 16/303,915

(22) PCT Filed: May 23, 2017

(86) PCT No.: PCT/IB2017/053035
§ 371 (c)(1),
(2) Date: Nov. 21, 2018

(87) PCT Pub. No.: WO2017/203429
PCT Pub. Date: Nov. 30, 2017

(65) Prior Publication Data
US 2020/0121752 A1  Apr. 23, 2020

(30) Foreign Application Priority Data
May 24, 2016 (ES) ................ ES201630673

(51) Int. Cl.
| | |
|---|---|
| A61K 36/87 | (2006.01) |
| A23L 33/105 | (2016.01) |
| A61K 8/9789 | (2017.01) |
| A61Q 19/00 | (2006.01) |
| C14C 3/00 | (2006.01) |
| C14C 3/08 | (2006.01) |
| C14C 3/12 | (2006.01) |

(52) U.S. Cl.
CPC ............ *A61K 36/87* (2013.01); *A23L 33/105* (2016.08); *A61K 8/9789* (2017.08); *A61Q 19/00* (2013.01); *C14C 3/00* (2013.01); *C14C 3/08* (2013.01); *C14C 3/12* (2013.01); *A61K 2800/10* (2013.01); *A61K 2800/43* (2013.01); *A61K 2800/522* (2013.01)

(58) Field of Classification Search
CPC ........................................... A61K 36/87
See application file for complete search history.

(56) References Cited

U.S. PATENT DOCUMENTS

| | | | |
|---|---|---|---|
| 5,912,363 A | 6/1999 | Nafisi-Movaghar et al. | |
| 6,479,081 B2 | 11/2002 | Feries | |
| 6,544,581 B1 * | 4/2003 | Shrikhande | C09B 61/00 426/655 |

FOREIGN PATENT DOCUMENTS

| | | |
|---|---|---|
| DE | 19827179 A1 | 12/1999 |
| ES | 2197821 A1 | 1/2004 |
| ES | 2443547 A1 | 2/2014 |
| FR | 2773150 B1 * | 3/2000 ............. C07C 37/82 |

OTHER PUBLICATIONS

Murga et al. J. Agric. Food Chem. 2000, 48, 3408-3412 (Year: 2000).*
International Search Report for PCT application PCT/IB2017/053035; European Patent Office; Rijswijk, Netherlands; dated Aug. 1, 2017.
Written Opinion of the International Searching Authority for PCT application PCT/IB2017/053035; European Patent Office; Munich, Germany; dated Aug. 1, 2017.
Frederique Bertaud et al.; "Development of Green Adhesives for Fibreboard Manufacturing, Using Tannins and Lignin from Pulp Mill Residues", Cellulose Chemistry and Technology; Jan. 1, 2012.
Susana Chamorro et al.; "Changes in polyphenolic content and antioxidant activity after thermal treatments of grape seed extract and grape pomace", European Food Research and Technology; Nov. 19, 2011.
International Preliminary Report on Patentability corresponding to International Patent Application No. PCT/IB2017/053035 dated Nov. 27, 2018.
Murga et al. (2000) "Extraction of Natural Complex Phenols and Tannins froln Grape Seeds by Using Supercritical Mixtures of Carbon Dioxide and Alcohol," J. Agric. Food Chem. vol. 48; pp. 3408-3412.

* cited by examiner

*Primary Examiner* — Russell G Fiebig
(74) *Attorney, Agent, or Firm* — Jenkins, Taylor & Hunt, P.A.

(57) ABSTRACT

A process for obtaining a tannin extract isolated from whole grape seeds is provided. The process is performed in as a one-pot reaction and in a single extraction step, wherein the seeds are processed without grinding or milling. Also provided is a tannin extract with improved antioxidant and light fastness properties obtained from whole grape seeds that includes a mixture of tannins and non-tannins, in which the content of tannins or polyphenols is higher than 50%. Ise, the tannin extract isolated from whole grape seeds can include a coloring agent.

15 Claims, 6 Drawing Sheets

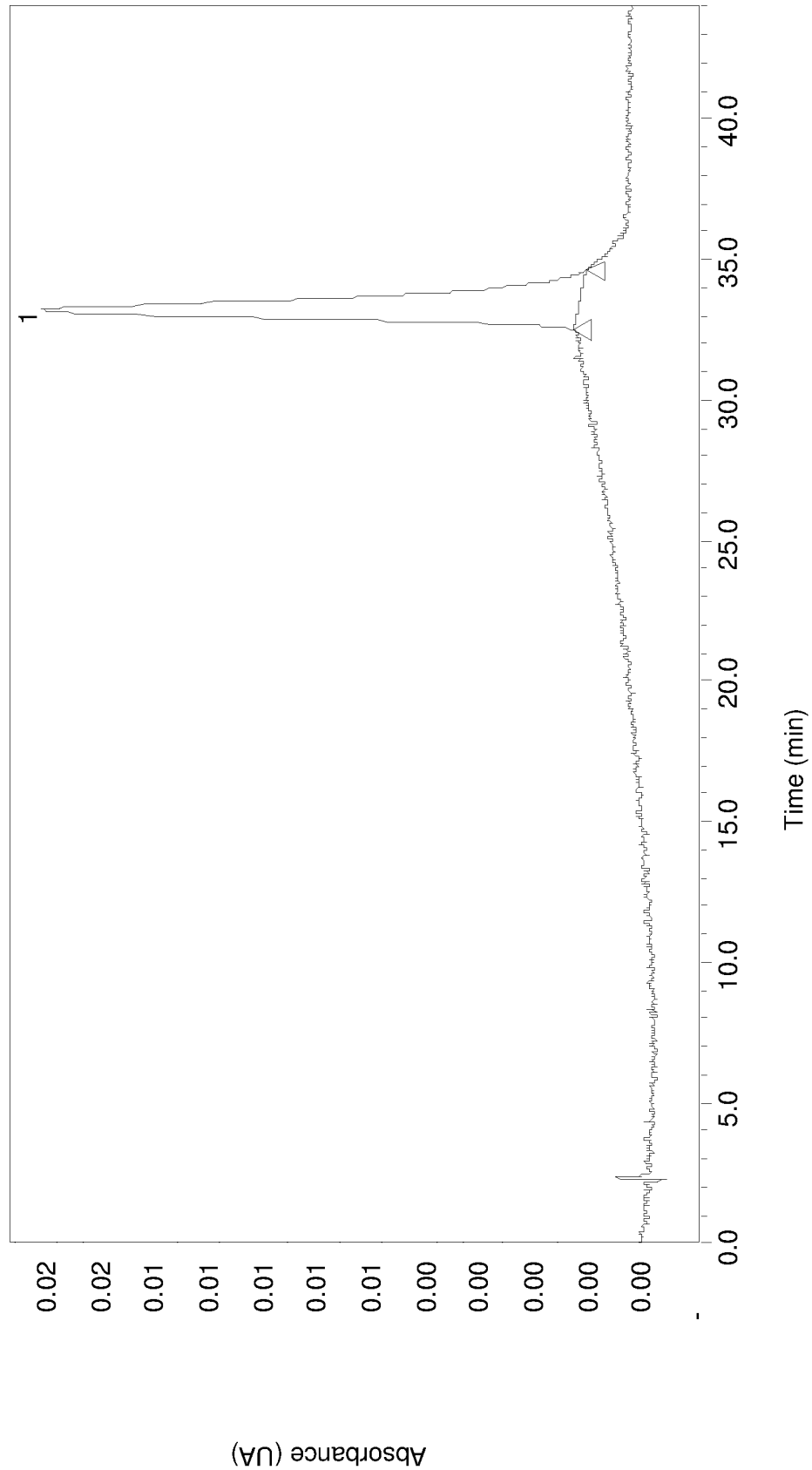

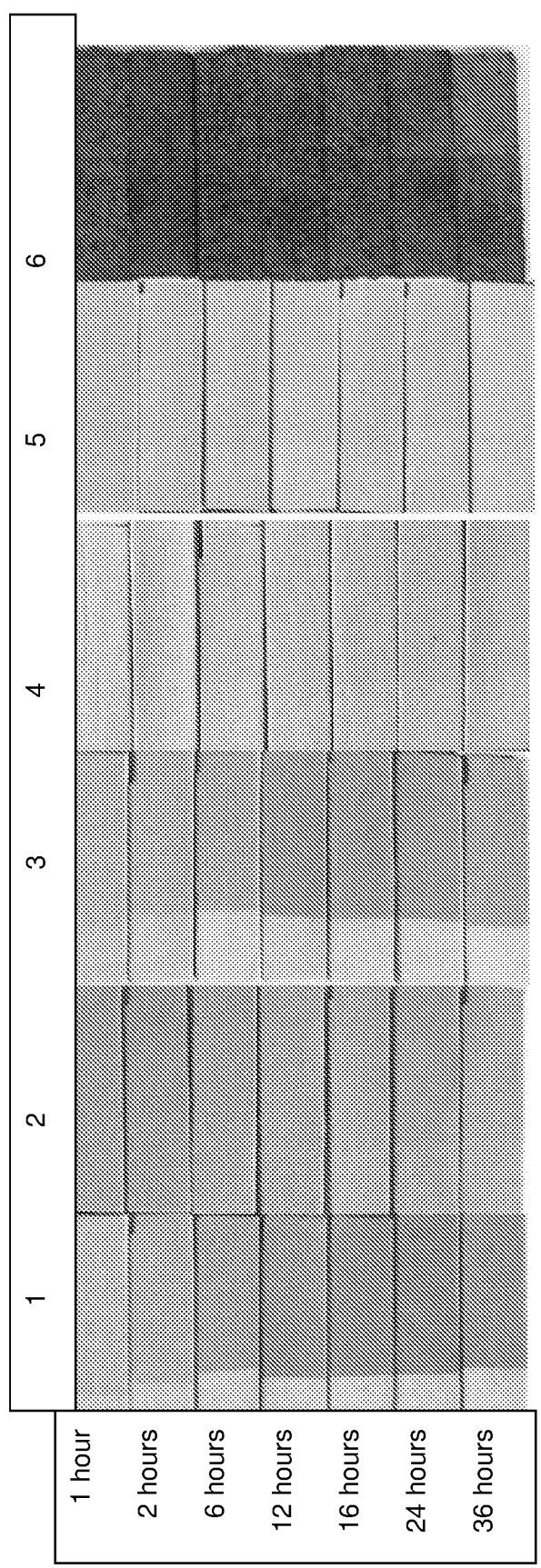

PROCESS FOR OBTAINING A TANNIN EXTRACT ISOLATED FROM GRAPES, TANNIN EXTRACT OBTAINED AND USES THEREOF

CROSS-REFERENCE TO RELATED APPLICATIONS

This is a § 371 National Stage Entry application of International Application Serial No. PCT/IB2017/053035, filed on May 23, 2017, which claims the benefit of Spanish Application No. 201630673, filed on May 24, 2016, the disclosures of which are hereby incorporated by reference.

FIELD OF THE INVENTION

The present invention relates to a process for obtaining a tannin extract isolated from grapes. In particular, the invention relates to an aqueous extraction process for obtaining a tannin extract which focuses on the source of tannins selected and the type of polyphenol-dissolving agent used in the extraction step.

The invention also relates to the tannin extract obtained through the steps defined in the process. In particular, a new tannin extract isolated from grape seeds is obtained which comprises a mixture of tannins and non-tannins, the composition whereof provides the extract with improved antioxidant and light fastness properties. The tannin extract isolated from grape seeds further comprises a colouring agent.

The invention also relates to the use of the tannin extract isolated from grape seeds as a tanning agent, antioxidant agent and/or colouring agent in the tanning, food, cosmetics and/or pharmaceutical industries.

BACKGROUND

The current vegetable tannin extraction technology designed for the tanning industry is based on extraction processes in the aqueous phase. The tannin extracts obtained are used in the tanning industry by causing them to react with the animal skin tissue, thereby preserving its flexibility and making it resistant to putrefaction.

The vegetable tannin extracts currently used in the tanning industry are primarily Quebracho Tree extract, Mimosa extract, Chestnut Tree extract, and Tara extract, all of them of vegetable origin, obtained from trees found in South American or South African forests which have been cultivated and cut down for this purpose.

Thus far, the raw materials used as the source of tannins have been ground woods, barks, leaves or other parts of trees. After the grinding, the resulting ground material is mixed in an alcoholic or aqueous solution, and an extraction is performed at a given pressure and temperature in order to extract the tannins from the raw material. The liquid fraction resulting from the extraction contains the tannins of interest. Separation of the solid fraction from the liquid fraction is performed by means of sedimentation, optionally followed by a chemical treatment, and, finally, the tannins are concentrated in order to obtain the vegetable tannin extract in the liquid state. When it is desired to obtain the extract in the solid state, a spraying step is also performed.

Different variants of this methodology have been proposed, for example, using cold water or hot water, at atmospheric pressure or higher.

Tannins are polyphenols, generally water-soluble, with a molecular weight ranging between 500 and 3,000, and a different composition depending on their origin, although with the approximate formula: $C_{14}H_{14}O_{11}$. Tannins have a characteristic odour, a colour that varies between yellowish to dark brown, they all have a bitter taste, are astringent, exposure to light darkens them and they react with ferric salts to form blue-black compounds that are used as a raw material to obtain colouring agents. Their main chemical characteristic is the capacity to precipitate proteins and make them resistant to decomposition, for which reason they are useful as tanning agents.

Spanish patent application ES2197821 discloses a process for obtaining a vegetable tannin extract in the aqueous phase. The source of tannins used is grape pomace, the grape pomace comprising a ground mixture of stalks, skin and seeds.

The process includes the following steps:
i) using grape pomace as the source of tannins;
ii) preparing a solution of a sulphonating agent in a certain quantity of water;
iii) simultaneously mixing the solution prepared in step ii) with the grape pomace from step i) in a reactor, at a given pressure and temperature, in order to extract the tannins;
iv) solid-liquid separation; and
v) purifying and concentrating the extract obtained.

According to the description in patent ES2197821A1, the tannins obtained from grape pomace are of the condensed type (catechinic) and their concentration is related to the number of extractions performed. Also described are a filtration step and a pressing step following the solid-liquid separation step, by discharging the liquid extracted, and, subsequently, a sedimentation and decantation step following the filtration and prior to the purification and concentration. Thus, in order to obtain acceptable extraction yields, it is necessary to perform additional steps and use different equipments, which makes industrial-scale production difficult.

Therefore, the method disclosed in ES2197821 is not feasible at industrial scale, partly because it requires a filtration step followed by a purification step in order to isolate the product of interest, and partly because the tannin extraction yield depends on the number of extractions performed—the greater the number, the greater the quantity of tannins extracted—, in addition to requiring different equipments.

By the other hand, Spanish patent application ES2443547 discloses a process for obtaining a vegetable tannin extract in a solvent phase comprising glicols and dispersants in order to prevent aggregation of the raw material employed as tannin source. The organic extraction process requires a fermentation for days and the addition of acids to stop said fermentation, and then solvent evaporation to obtain the extract. The yields provided by this methods are very low and therefore this method is not suitable to be use at industrial scale.

Consequently, it would be desirable to provide a process for obtaining a vegetable extract that is environmentally friendly, scalable to industrial scale, simple and easy, with good yields, in order to produce tannin extract that is soluble or dispersible in cold water, with improved antioxidant and light fastness properties. Moreover, an extract of vegetable origin with colouring properties is desirable.

SUMMARY

In order to resolve the problems posed in the prior art, the present invention focuses on the source of tannins selected and the type of polyphenol-solubilising agent used in the extraction step. The adequate processing of both, using certain steps and conditions, provides a new extract isolated from grapes.

Thus, a first aspect of the invention has the purpose of providing an aqueous extraction process for obtaining a tannin extract isolated from grapes which comprises using a source of tannins, preparing an aqueous solution of a polyphenol-solubilising agent and a tannin extraction step in a reactor that comprises the source of tannins and the previously-prepared aqueous solution at a given pressure and temperature, characterised in that:

the source of tannins consists of grape seeds,
the polyphenol-solubilising agent is selected from urea, sodium hydroxide and a compound containing the $SO_3$ group, and its concentration in the aqueous solution ranges between 1% and 15% by weight with respect to the weight of the grape seeds, and
the extraction step is performed in an autoclave at a pressure ranging between 1 and 6 atmospheres and a temperature ranging between 80° C. and 160° C., and
optionally, concentration of the extract by evaporation, to obtain the concentrated isolated tannin extract, and/or spray drying, to obtain the isolated tannin extract in the solid state.

Surprisingly, the process of the present invention allows to provide a very high content of tannins or polyphenols in the obtained tannin extract, as high as, and higher than 50% in a one-pot extraction, and in a single extraction step.

In the present invention, the term "grape seed" is understood to mean the pip or kernel separated from the grape berry and dried. Therefore, the weights calculated for the grape seeds are dry weights. The shape of the pips or kernels may be ovoid, spherical, flat or circular, and they may have various sizes. The hardness ranges from soft to crunchy. The pip or kernel is inside the grape berry, and is in charge of the reproductive pathway in vines.

Preferably, the grape seeds are used whole, i.e. grape seeds or kernels that have not been ground or milled are preferred. The authors of the present invention have found better properties in the extract obtained and better process yields using whole grape seeds.

In the present invention, the term "polyphenol-solubilising agent" is understood to mean an agent capable of reacting with the carboxylic groups present in polyphenols. In the present invention, said polyphenol-solubilising agent is selected from urea, a compound containing the $SO_3$ group or sodium hydroxide. The compound containing the $SO_3$ group is an inorganic acid or salt that contains the $SO_3$ group, such as sulfuric acid, oleum, sulfamic acid, sodium sulfite, sodium bisulfite or sodium metabisulfite.

In a preferred embodiment, the polyphenol-solubilising agent is urea.

Preferably, the concentration of the polyphenol-solubilising agent in the aqueous solution ranges between 2% and 8% by weight with respect to the weight of the grape seeds.

Preferably, the weight ratio between the grape seeds and the water used to prepare the solution is 1:1. However, this ratio may vary between 0.5:1 and 1:4.

Also preferably, the extraction step is performed in an autoclave reactor at a temperature ranging between 100° C. and 130° C., and a pressure ranging between 2.5 and 3.5 atmospheres. Even more preferably, the extraction step is performed at a temperature of 120° C.±2° C. and a pressure of 3 atmospheres. These extraction conditions are maintained for a period of time ranging between 1 and 2 hours. The liquid extract obtained may be used directly for the tanning of hides and skins.

In the present invention, the term "autoclave" is understood to mean a reaction chamber. This reaction chamber, which is usually made of stainless steel, is designed to operate at high pressures in order to perform a reaction, baking or sterilisation with water vapour. Using a high pressure, of up to approximately 6 atmospheres, makes it possible for the water to reach temperatures higher than 100° C.

Thus, a first aspect of the present invention provides a simple, easy process that only requires an autoclave reactor and a single extraction step in order to obtain good yields, as compared to the prior art, which requires filtration and purification, in addition to several extractions in order to obtain an acceptable yield.

Advantageously, the process for obtaining the tannin extract isolated from grape seeds of the first aspect provides high yields, 63% and 80.3%, as compared to 42.1% in the prior art.

A process is provided that is environmentally friendly, reuses the grape seeds and the grape subproducts or residues, which are widely available and easy to obtain due to their geographical concentration, without the need to cut down trees or import parts thereof.

A process is provided that is scalable to industrial scale, uses shorter processing times and does not require filtration, sedimentation, decantation, or purification, steps which are not desirable in an industrial-scale process.

Moreover, the process according to the first aspect of the invention is designed such that, if so desired, the water used to clean the autoclave reactor may be reused, thereby reducing water consumption by up to 80% of the total water consumption. Advantageously, the water used to clean the equipment is susceptible to being reused as a component in the preparation of the aqueous solution of the polyphenol-solubilising agent for a new extraction.

Advantageously, the process for obtaining an extract isolated from grapes according to the first aspect of the invention reduces the energy consumption necessary to obtain the extract, because the costs of the steps for the extraction and concentration of the grape seed tannins are lower, as no additional separation steps or purification steps for the extract obtained are required.

Surprisingly, by means of the process according to the first aspect of the present invention, a new tannin extract isolated from grapes is obtained.

Thus, a second aspect of the present invention relates to a tannin extract isolated from grapes obtained according to the first aspect of the invention, which comprises a mixture of pure hydrolysable tannins, pure condensed tannins that include procyanidins and non-tannins that include gallic acid.

The vegetable extracts are primarily composed of four fractions, namely:

a) Non-Tannins: This is the fraction with a low molecular weight, lower than 500, which does not have tanning power but contributes to improving the solubility of the tannin, increasing the penetration rate and separating the fibres from the skins.

b) Tannins: These are water-soluble polyphenols with a molecular weight ranging between 500 and 3,000, a different composition depending on their origin, but with an approximate formula $C_{14}H_{14}O_{11}$. Tannins have a characteristic odour, a colour that varies from yellowish to dark brown, they all have a bitter taste, are astringent, exposure to light darkens their colour and they react with ferric salts to produce blue-black compounds that are used to make dyes. Their main chemical characteristic is the capacity to precipitate proteins and make them resistant to decomposition, which is what determines their use as a tanning agent. On the basis of their structural characteristics, tannins are classified into:

Hydrolysable or pyrogallic tannins: Those that, in the presence of strong acids and at high temperatures, are hydrolysed into glucose and gallic acid or ellagic acid, to produce gallotannins or ellagitannins. The former are extracted from galls, *Quercus infectoria* and *Rhus semisalata*, from sumac leaves, *Rhus coriaria*, and the tara *Caesalpinia spinosa*, whereas ellagitannins are present in oak wood, *Quercus robur*, *Quercus petraea* and *Quercus alba*, chestnut tree, *Castanea vesca* and *Castanea dentae*, and myrobalan, *Terminalia chebula.*

Condensed or catechinic tannins: Condensed tannins are not decomposed by acids and are characterised by their gradual capacity to form insoluble polymerisates called flavonoids. They are differentiated into proanthocyanic tannins, which, by means of acid hydrolysis, release anthocyanins and other compounds, and profisetinidic tannins, which are present in extractions from woods of the quebracho tree, *Schinopsis balasae* and *Schinopsis lorentzii*, mimosa, *Acacia mearnsi* and *Acacia mollissima*, and gambir leaves, *Uncaria-gambi.*

There are tannins whose structure is a mixture of hydrolysable and condensed tannins.

c) Insoluble: This is the fraction with a molecular weight greater than 3,000, which corresponds to very astringent polyphenol-carbohydrate complexes that, due to their high molecular weight, have difficulties in penetrating the skin and are superficially fixed. Their presence is not desirable and, in fact, they are found in extracts manufactured under very aggressive conditions.

d) Humidity: Percentage of water in each extract.

Surprisingly, the combination of different types of polyphenols present in the extract obtained according to the first aspect of the invention provides it with improved light fastness properties and antioxidant properties as compared to the vegetable extracts in the prior art.

Unexpectedly, when urea is used as the polyphenol-solubilising agent in the process for obtaining the extract, the tannin extract obtained comprises a colouring agent. Therefore, the tannin extract isolated from grape seeds obtained using urea as the polyphenol-solubilising agent comprises a mixture of pure hydrolysable tannins, pure condensed tannins that include procyanidins, non-tannins that include gallic acid and shows a maximum at 352.8 nm, 2.70 A, measured by UV-Vis spectroscopy between 350-800 nm, indicating the presence of a colouring agent in the UV region.

The authors of the present invention performed UV-Vis spectrophotometry assays (350-800 nm) in a sample extract obtained using urea as the polyphenol-solubilising agent to prepare the aqueous solution, which was compared to the scan of a conventional brown colouring agent, specifically Dark Brown CA, which appears at 472.85 nm, and the results of the scan show a maximum in the sample extract at 352.8 nm, Absorbance 2.70 A, within the UV region (see FIG. 4).

The authors of the present invention have corroborated the presence of said colouring agent by means of an HPLC analysis of the sample extract, as it is shown in the chromatogram depicted in FIG. 5.

Thus, the invention also provides an extract that comprises an azo colouring agent, wherein said azo colouring agent is free of, or has a limit of detection lower than 30 mg/kg for, banned aromatic amines, which makes it suitable to be used as a tanning agent, antioxidant agent and colouring agent in the tanning, food, cosmetics and/or pharmaceutical industries, as desired.

In the present invention, "colouring agent without, or free of, banned aromatic amines" is understood to mean that said aromatic amines are not detected with a limit of detection of 30 mg/kg.

A third aspect of the invention relates to the use of the tannin extract according to the first or second aspects of the invention as a tanning agent, antioxidant agent, or colouring agent in the tanning, food, cosmetics or pharmaceutical industries.

One additional advantage of the new extract is its multifunctionality, since it has applications as an antioxidant agent, a colouring agent and a tanning agent.

Moreover, the extract of the invention may also be used in combined chrome-vegetable tanning or as a retanning agent in already chrome-tanned skins and leathers that require a treatment after tanning in order to modify characteristics such as the resistance, the thickness or the flexibility.

Food Use

In the wine industry, tannins are responsible for such important sensory characteristics as the colour, the body, the astringency and the bitterness. The origin of said compounds lies in the raw material with which wine is elaborated, but also in the oak wood used in barrel ageing or directly applied to the wine. In the case of oak barrels, there are tannins known as hydrolysable tannins (both classes, ellagitannins and gallotannins), to differentiate them from those of the grapes, which have a higher concentration of condensed tannins; the latter significantly contribute to positive wine aspects, such as the body and the colour stability of red wines. The precipitation properties of tannins are used to clean up or clarify wines or beer.

Advantageously, using the tannin extract obtained from grape seeds according to the invention, an extract is obtained with a composition that makes it useful for food use, for example, in the wine industry.

Industrial Use

In industry, tannins are primarily used in the tanning of skins, thanks to their capacity to transform proteins into products that are resistant to decomposition. During this tanning process, certain tannins are used; the most widely used are those from acacias, chestnut trees, holm oaks, pine trees or bastarda chestnut trees. They are also used in the textile industry, due to their capacity to react with ferric salts, which leads to blue-black products that are suitable for dyes. They are also used as mordants for the application of dyes to fabrics, rubber coagulants, or paper or silk hardeners.

Advantageously, using the tannin extract obtained from grape seeds according to the invention, an extract is obtained with a composition that makes it useful for industrial use, for example, in the tanning industry.

Medicinal Use

In medicine, they are prescribed due to their astringent, haemostatic, antiseptic and toning actions. The aforementioned property of coagulating the albumins in mucous membranes and tissues creates a dry, insulating and protective layer that reduces skin irritation and pain. Externally, preparations based on tannin-rich drugs, such as decoctions, are used to stop small local haemorrhages, in inflammations of the buccal cavity, colds, bronchitis, burns, haemorrhoids, etc. Internally, they are useful against diarrhoea, stomach flu and vesicular diseases. Tannins are also useful as antidotes in the case of intoxication caused by vegetable alkaloids.

BRIEF DESCRIPTION OF THE SEVERAL VIEWS OF THE DRAWINGS

In order to contribute to a better understanding of what has been explained above, a set of drawings is attached wherein, schematically and only as a non-limiting example, an embodiment is represented.

FIG. 5 shows the chromatogram, obtained by means of HPLC-DAD at 500 nm, of a sample extract obtained according to Example 2 of the invention within the 200-800 nm range.

FIG. 6 shows a comparative assay of the artificial light fastness according to the IUF 402 standard, wherein we may observe the stability of the extract obtained according to Example 1 and Example 2 of the invention.

DETAILED DESCRIPTION

In order to contribute to a better understanding of what has been explained above, some examples are attached wherein, schematically and only as non-limiting examples, specific embodiments of the invention are represented.

EXAMPLES

Example 1: Tannin Extract Isolated from Grape Seeds

Chemical Extraction

For 100 kg of whole dried grape seeds, 5 kg of sodium metabisulfite and 100 litres of distilled water were used. The aqueous solution contained 5% of sodium metabisulfite.

All the components were introduced into an autoclave reactor and the aqueous extraction was performed therein, keeping the temperature at 120° C. and the pressure at 3 atmospheres for 1 hour.

Once the specified time had elapsed, a tannin extract isolated from grape seeds in the liquid state suitable for the tanning of skins was obtained.

Example 2: Tannin Extract Isolated from Grape Seeds

Chemical Extraction

For 100 kg of whole dried grape seeds, 5 kg of urea and 100 litres of distilled water were used. The aqueous solution contained 5% of urea.

All the components were introduced into an autoclave reactor and the aqueous extraction was performed therein, keeping the temperature at 120° C. and the pressure at 3 atmospheres for 1 hour.

Once the specified time had elapsed, a tannin extract isolated from grape seeds in the liquid state suitable for the tanning of skins was obtained.

Example 3 (Reference Example): Tannin Extract Isolated from Grape Pomace

Chemical Extraction

For 200 kg of pomace, 2 kg of sodium metabisulfite and 400 litres of distilled water were used.

All the components were introduced into an autoclave reactor and the aqueous extraction was performed therein, keeping the temperature at 136° C. and the pressure at 5 atmospheres for 3 hours.

Once the specified time had elapsed, the tannin extract isolated from pomace was obtained.

Assays

Chromatography of the Extracts Obtained According to Examples 1 to 3

Figure 1:
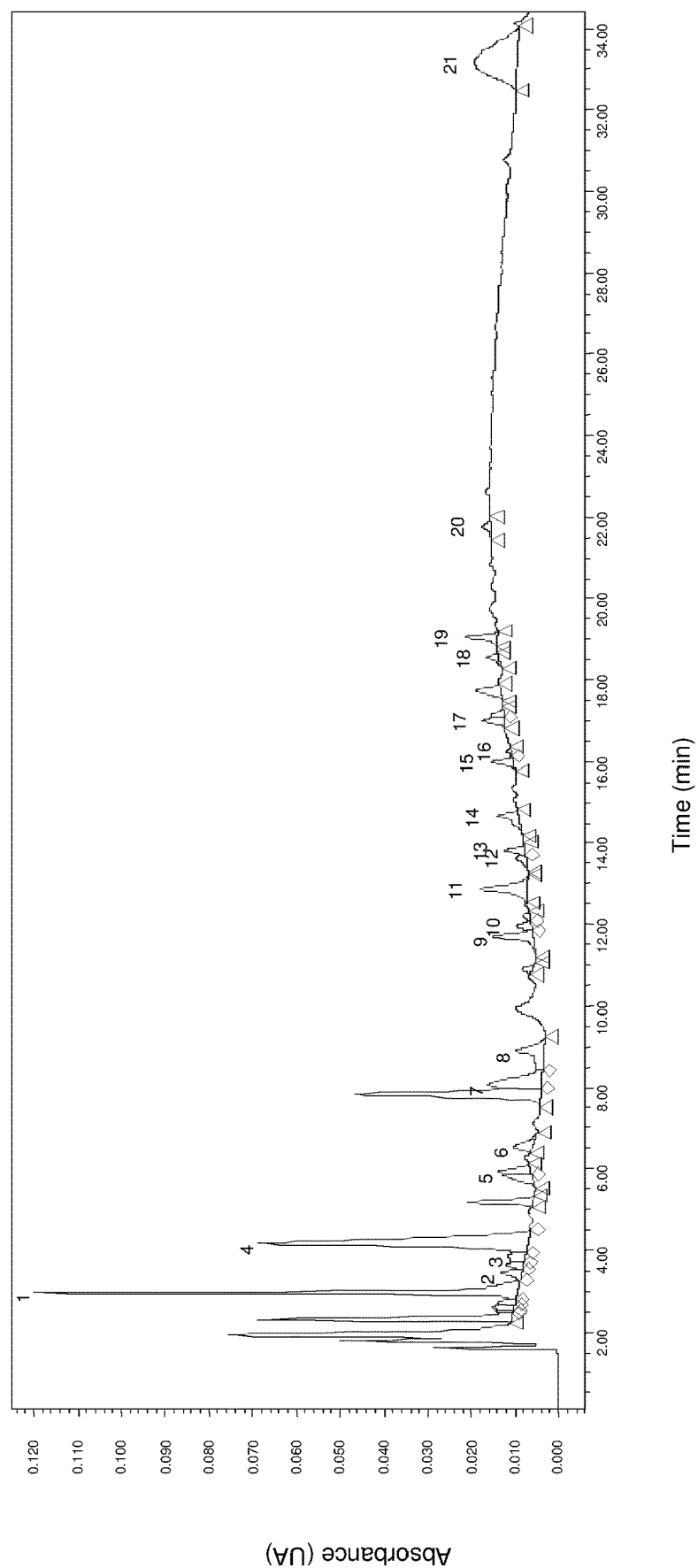
FIG. 1 shows the chromatogram, obtained by means of reverse-phase high-performance liquid chromatography (HPLC), of the extract obtained according to the first and second aspects of the invention, wherein the source of tannins are whole grape seeds and the polyphenol-solubilising agent used in the extraction step is sodium metabisulfite according to Example 1 of the invention.
Figure 2:
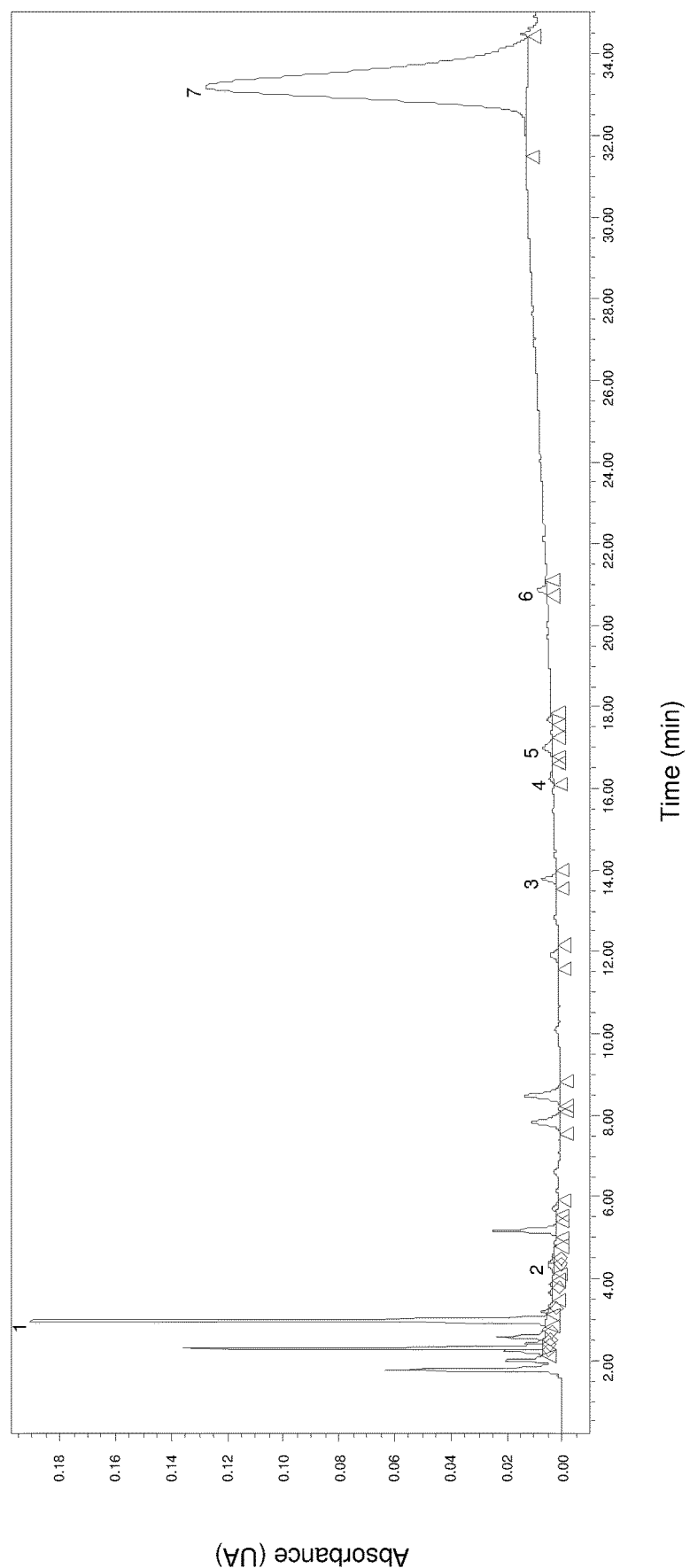
FIG. 2 shows the chromatogram, obtained by means of reverse-phase high-performance liquid chromatography (HPLC), of an extract obtained according to the first and second aspects of the invention, wherein the source of tannins are whole grape seeds and the polyphenol-solubilising agent used in the extraction step is urea according to Example 2 of the invention.
Figure 3:
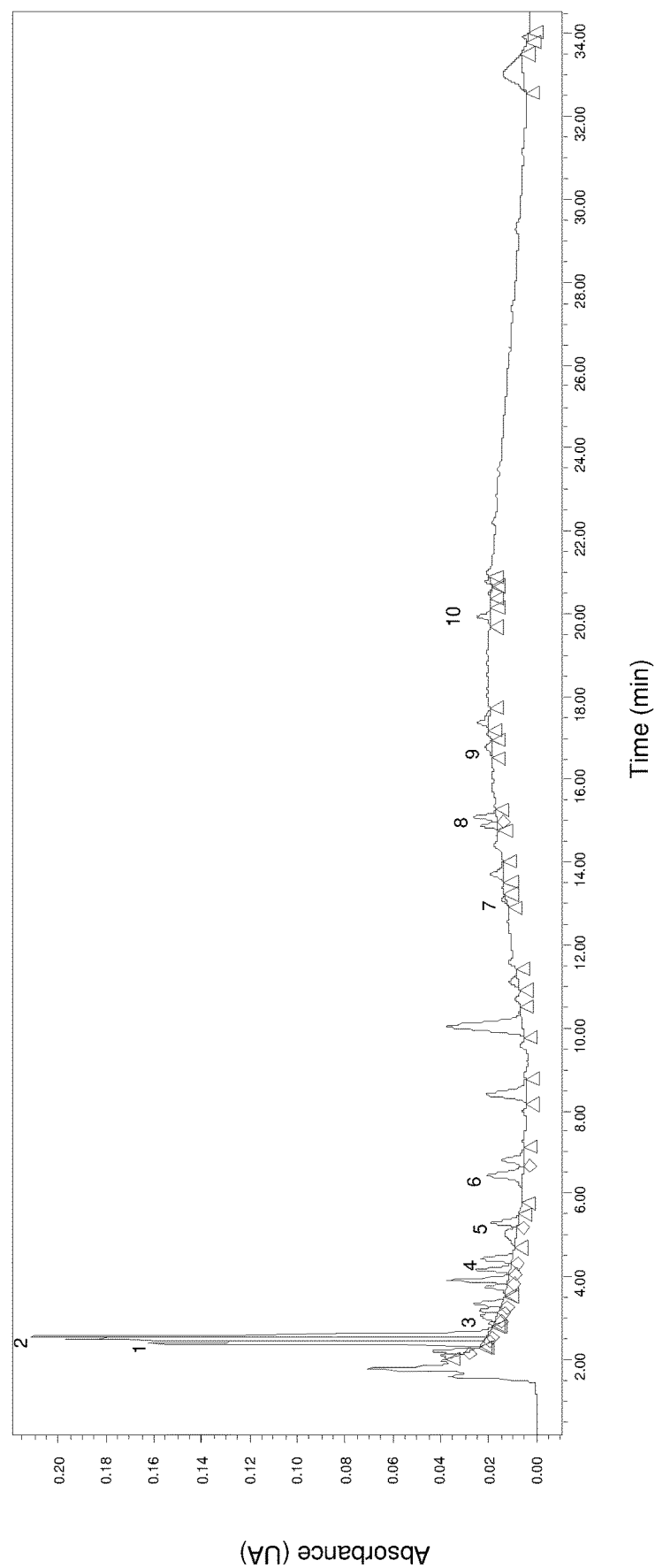
FIG. 3 shows the chromatogram, obtained by means of reverse-phase high-performance liquid chromatography (HPLC), of the extract obtained according to reference Example 3, wherein the source of tannins is ground grape pomace and the polyphenol-solubilising agent used in the extraction step is sodium metabisulfite.

The extracts obtained Examples 1 to 3 were analysed by means of high-performance column chromatography with reverse-phase separation HPLC-DAD. A column of the Xbridge Phenyl type was used. For the chromatographic analysis, a 1:25 aqueous solution of the extracts obtained in the examples was prepared. Subsequently, the extracts were filtered to 0.45 µm in order to be analysed. 25 µl of the extract were injected. The chromatogram capture wavelength was 271.1 nm. See FIGS. 1 to 3, which correspond, respectively, to Examples 1 to 3.

For the analysis, a new spectral library was generated wherein the spectra of the different compounds present in commercial Mimosa, Quebracho Tree, Tara and Chestnut Tree tannin samples were incorporated. The spectra of commercial polyphenol standards with different chemical natures, including the condensed, or catechinic, types and the hydrolysable type, or gallotannins, were also incorporated. Below we show a list of the standards studied by means of the chromatographic separation method defined in the invention:

| Compound | CAS N° | Category | MW | Retention time (min) | (R²) |
|---|---|---|---|---|---|
| (+)-Catechin | 154-23-4 | Flavan-3-ol | 290.3 | 11.8 | 0.9983 |
| (−)-Epicatechin | 490-46-0 | Flavan-3-ol | 290.3 | 16.1 | 0.9985 |
| (−)-Epigallocatechin | 970-74-1 | Flavan-3-ol | 306.3 | 10.3 | 0.9998 |
| (−)-Epicatechin gallate | 2157-08-5 | Flavan-3-ol | 442.4 | 22.7 | 0.9979 |
| (−)-Epigallocatechin gallate[(1)] | 959-51-5 | Flavan-3-ol | 458.4 | 17.3 | n.c. |
| Procyanidin B1 | 20315-25-7 | Procyanidin Dimer | 578.5 | 10.9 | 0.9999 |
| Procyanidin B2 | 29106-49-8 | Procyanidin Dimer | 578.5 | 15.4 | 0.9503 |
| Procyanidin A2 | 20315-25-7 | Dimeric Catechin | 576.5 | 23.7 | 0.9535 |
| Penta-O-galloil-B-D-glucose[(1)] | 14937-32-7 | Gallotannin | 940.7 | 25.1 | n.c. |

Summary of the standards analysed by means of reverse-phase HPLC-DAD.
[(1)]n.c. (no correlation).

The compounds identified in the extracts obtained according to Example 1, Example 2 and reference Example 3 were then compared.

Table 1 below lists the compounds identified in the tannin extract isolated from grape seeds according to Example 1:

| Peak | RT (min) | Identification | Surface area | % Surface area/ Total surface area |
|---|---|---|---|---|
| 1 | 2.97 | Gallic Acid standard | 590,723 | 16.1 |
| 2 | 3.46 | Catechinic tannin from Quebracho Tree 1 | 43,598 | 1.2 |
| 3 | 3.87 | Catechinic tannin from Mimosa 1 | 51,787 | 1.4 |
| 4 | 4.17 | Catechinic tannin. (Same chromophore as Procyanidin B2) | 753,881 | 20.5 |
| 5 | 5.93 | Catechinic tannin. (Same chromophore as (+)-Catechin) | 62,630 | 1.7 |
| 6 | 6.54 | Catechinic tannin from Mimosa 2 | 55,427 | 1.5 |
| 7 | 8.07 | Catechinic tannin from Mimosa 3 | 193,423 | 5.3 |
| 8 | 8.91 | Catechinic tannin. (Same chromophore as Procyanidin B2) | 124,261 | 3.4 |
| 9 | 11.71 | Catechinic tannin. (Same chromophore as (−)-Epicatechin) | 92,394 | 2.5 |
| 10 | 11.96 | Catechinic-hydrolysable tannin. (Same chromophore as (−)-Epigallocatechin gallate) | 32,164 | 0.9 |
| 11 | 12.88 | Catechinic-hydrolysable tannin. (Same chromophore as (−)-Epicatechin gallate) | 138,372 | 3.8 |
| 12 | 13.63 | Catechinic tannin from Mimosa 4 | 26,330 | 0.7 |
| 13 | 13.83 | Gallic tannin from Tara 1 | 38,722 | 1.1 |
| 14 | 14.67 | Catechinic-hydrolysable tannin. (Same chromophore as (−)-Epigallocatechin gallate) | 60,524 | 1.6 |
| 15 | 15.99 | (−)-Epicatechin standard | 38,685 | 1.1 |
| 16 | 16.25 | Catechinic tannin. (Same chromophore as (−)-Epicatechin) | 6,683 | 0.2 |
| 17 | 17.01 | Tannin derived from gallic acid | 46,040 | 1.3 |
| 18 | 18.57 | Catechinic-hydrolysable tannin. (Same chromophore as (−)-Epicatechin gallate) | 22,905 | 0.6 |
| 19 | 19.07 | Catechinic-hydrolysable tannin. (Same chromophore as (−)-Epigallocatechin gallate) | 63,283 | 1.7 |
| 20 | 21.78 | (−)-Epicatechin gallate standard | 23,363 | 0.6 |
| 21 | 33.17 | Catechinic tannin from Quebracho Tree 2 | 502,689 | 13.7 |

Table 2 below shows the compounds identified in the tannin extract isolated from grape seeds according to Example 2:

| Peak | RT (min.) | Identification | Surface area | % Surface area/ Total surface area |
|---|---|---|---|---|
| 1 | 2.97 | Gallic Acid standard | 842,937 | 12.2 |
| 2 | 4.39 | Catechinic tannin. (Same chromophore as (−)-Epicatechin) | 11,218 | 0.2 |
| 3 | 4.57 | Catechinic tannin. (Same chromophore as Procyanidin A2) | 6.173 | 0.1 |
| 4 | 13.79 | Gallic tannin from Tara 1 | 42,495 | 0.6 |
| 5 | 16.25 | (−)-Epicatechin standard | 14,799 | 0.2 |
| 6 | 17.00 | Gallic tannin from Tara 2 | 35,618 | 0.5 |
| 7 | 17.68 | Catechinic tannin. (Same chromophore as Procyanidin A2) | 11.152 | .02 |
| 8 | 20.87 | Ellagic Acid | 26,598 | 0.4 |
| 9 | 33.20 | Catechinic tannin from Quebracho Tree 2 | 5,452,782 | 79.0 |

The present invention refers to the chromatographic analysis of an aqueous polyphenolic extract that includes tannins, non-tannins and unidentified compounds differentiated as such on the basis of the HPLC-DAD assay of the diluted polyphenolic extract using the specified assay method. Tannins or polymers with a tanning capacity are considered to be those polymer molecules with a molecular weight greater than 500. A semi-quantitative estimate of the content of each component is included, calculated from the surface area percentage of each peak with respect to the total surface area. In Example 1 and Example 2, we may observe the peaks identified due to their spectral similarity with the substances present in the spectral library. The peaks identified in the chromatogram belong to the Grape Tannin library entries corresponding to the polyphenol standards cited in Table 1, samples of commercial vegetable tannin from Tara and commercial vegetable extracts from Mimosa, Quebracho Tree and Chestnut Tree.

Condensed tannins are polymers formed by units of anthocyanidin (flavonoid). Since they may be hydrolysed into their constituent anthocyanidins when treated with strong acids, they are sometimes known as proanthocyanidins.

The invention presents tanning polyphenolic extracts whose tannin and non-tannin composition is mostly determined by means of the specified chromatographic separation method (80.8% of the total compounds for Example 1; 93.1% of the total compounds in Example 2). In fact, the presence of non-tannins expressed as a percentage is justified on the basis of the monomeric units identified through the retention times and the UV-Vis spectra of the corresponding standards (gallic acid, (−)-epicatechin, (−)-epicatechin gallate). Said substances are not considered to be tannins since their molecular weight is less than 500.

Example 1

In the invention, the group of tannins or polyphenols with tanning capacity that have been referenced as condensed or catechinic (52.1%) include the following group of compounds:
The set of tannins separated in the chromatogram with respect to the total surface area of the compounds identified includes chromophoric polymers of the compound Procyanidin B2, which represent a total of 23.9%. 2 tannins are detected that contain the same chromophore group as procyanidin B2, since they present the same UV-Vis spectrum.
4 catechinic tannins present in the commercial Mimosa tannin at 8.9% are detected, corroborated because they have the same retention times and UV-Vis spectra as the peaks corresponding to the chromatogram of the commercial sample used as a standard.
4 catechinic tannins present in the commercial Quebracho Tree tannin at 14.9% are detected, corroborated because they have the same retention times and UV-Vis spectra as the peaks corresponding to the chromatogram of the commercial sample used as a standard.
1 catechinic tannin present at 1.7% is detected which contain the same chromophore group as the compound (+)-catechin, since it presents the same UV-Vis spectrum.
1 catechinic tannin present at 2.7% is detected which contain the same chromophore group as the compound (−)-epicatechin, since it presents the same UV-Vis spectrum.
In the invention, the group of tannins or polyphenols with tanning capacity that have been referenced as catechinic-hydrolysable (8.6%) includes the following group of compounds:
3 catechinic hydrolysable tannins present at 4.2% are detected which contain the same chromophore group as the compound (−)-Epigallocatechin gallate, since they present the same UV-Vis spectrum.
2 catechinic hydrolysable tannins present at 4.4% are detected which contain the same chromophore group as the compound (−)-Epicatechin gallate, since they present the same UV-Vis spectrum.
In the invention, the group of tannins or polyphenols with tanning capacity that have been referenced as hydrolysable (2.3%) includes the following group of compounds:
1 hydrolysable tannin present in the commercial Tara tannin at 1.1%, corroborated because it has the same retention time and UV-Vis spectrum as one of the peaks of the chromatogram of the commercial sample used as a standard.
1 hydrolysable tannin derived from gallic acid present at 1.3% that contains the same chromophore group as gallic acid, since they present the same UV-Vis spectrum.
In the invention, the group of non-tannins without tanning capacity that have been referenced as non-tannins (17.8%) includes the group of compounds identified as having the same retention times and UV-Vis spectra as the gallic acid, (−)-epicatechin and (−)-epicatechin gallate standards.

Example 2

In the invention, the group of tannins or polyphenols with tanning capacity that have been referenced as condensed or catechinic (79.2%) includes the following group of compounds:
1 catechinic tannin present in the commercial Quebracho Tree tannin at 79.0% is detected, corroborated because it has the same retention time and UV-Vis spectrum as one of the peaks of the chromatogram of the commercial sample used as a standard.
1 catechinic tannin present at 0.2% is detected that contains the same chromophore group as the compound (−)-Epicatechin, since they present the same UV-Vis spectrum.
2 tannins present at 0.3% is detected that contain the same chromophore group as the compound Procyanidine A2, since they present the same UV-Vis spectrum.
In the invention, the group of tannins or polyphenols with tanning capacity that have been referenced as hydrolysable (1.1%) includes the following group of compounds:
2 hydrolysable tannins present in the commercial Tara tannin at 1.1% are detected, corroborated because they have the same retention times and UV-Vis spectra as two of the peaks of the chromatogram of the commercial sample used as a standard.
In the invention, the group of non-tannins without tanning capacity that have been referenced as non-tannins (12.8%) includes the group of compounds identified as having the same retention times and UV-Vis spectra as the gallic acid, (−)-epicatechin and ellagic acid standards.
It is worth noting that the compounds identified in the tannin extract isolated from grape seeds in both Example 1 and Example 2 include a mixture of different types of tannins which comprises pure hydrolysable tannins, pure condensed tannins that includes procyanidins and non-tannins that include gallic acid and epicatechin.
Moreover, in one embodiment, the tannin extract isolated from grape seeds comprises a mixture of pure hydrolysable tannins, pure condensed tannins, tannins of the catechinic-hydrolysable type and non-tannins that include gallic acid.
The combination of the different types of tannins and the presence of gallic acid provide the extract with improved properties as compared to the properties of extracts in the prior art. Moreover, the extract may also contain a colouring agent in the UV region, which provides it with a multifunctionality that has not been previously described in the prior art.
Table 3 below lists the compounds identified in the tannin extract isolated from grape pomace according to reference Example 3:

| Peak | RT (min.) | Identification | Surface area | % Surface area/Total surface area |
|---|---|---|---|---|
| 1 | 2.39 | Catechinic tannin from Quebracho Tree A | 619,151 | 13.1 |
| 2 | 2.56 | Catechinic tannin from Quebracho Tree B | 921,371 | 19.5 |
| 3 | 3.05 | Catechinic tannin from Quebracho Tree C | 58,790 | 1.2 |
| 4 | 4.42 | Catechinic tannin. (Same chromophore as Procyanidin B2) | 97,276 | 2.1 |

-continued

| Peak | RT (min.) | Identification | Surface area | % Surface area/ Total surface area |
|---|---|---|---|---|
| 5 | 5.3 | Catechinic tannin from Mimosa 1. | 91,454 | 1.9 |
| 6 | 6.44 | Catechinic-hydrolysable tannin. (Same chromophore as (−)-Epicatechin gallate) | 186,980 | 4.0 |
| 7 | 13.09 | Catechinic tannin from Mimosa 2 | 14,589 | 0.3 |
| 8 | 15.1 | Gallic tannin from Tara 1 | 81,810 | 1.7 |
| 9 | 16.77 | Catechinic tannin from Mimosa 3 | 29,581 | 0.6 |
| 10 | 19.94 | Ellagic Acid | 45,466 | 1.0 |
| 11 | 33.03 | Catechinic tannin from Quebracho Tree 2 | 244,369 | 5.2 |

Table 4 is a summary table of the contents and types of tannins and non-tannins in the extracts obtained according to Examples 1 to 3:

| Tannins | Example 1 % Surface area/ Total surface area | Example 2 % Surface area/ Total surface area | Reference Example 3 % Surface area/Total surface area |
|---|---|---|---|
| Catechinic | 52.1 | 79.5 | 36.4 |
| Hydrolysable | 2.3 | 1.1 | 1.7 |
| Catechinic-Hydrolysable | 8.6 | 0 | 4.0 |
| Total | 63.0 | 80.6 | 42.1 |
| Non-Tannins | % Surface area/ Total surface area | % Surface area/ Total surface area | % Total surface area |
| Gallic Acid | 16.1 | 12.2 | 0 |
| Ellagic Acid | 0 | 0.4 | 1.0 |
| Catechinic | 1.7 | 0.2 | 7.7 |
| Total | 17.8 | 12.8 | 8.7 |
| Not identified | % Surface area/ Total surface area | % Surface area/ Total surface area | % Total Surface area |
| Total | 19.2 | 6.6 | 49.2 |

The percentage of catechinic tannins obtained from grape seeds is almost twice as much in one embodiment (Example 1) as in the prior art (reference Example 3) and more than twice as much (Example 2) as in the prior art (reference Example 3). The percentage of non-tannins that include gallic acid is similar in the two examples, 1 and 2, according to the invention, whereas they do not appear in reference Example 3. Although they do not have tanning power, the presence of non-tannins contributes to improving the solubility of tannins, increasing the penetration rate and separating the fibres from the skins. Therefore, an adequate balance between tannins and non-tannins in the extract isolated from grape seeds is responsible for the improved properties of the extract obtained according to the invention. Said balance is maintained in the extract obtained in Example 2, which further comprises the azo colouring agent.

UV-Vis Scan of the Extract Obtained in Example 2

The reference colouring agent used was Dark Brown CA.

The extract obtained according to Example 2 was compared to the reference colouring agent by means of a UV-Vis scan obtained between 350-800 nm using UV-Vis spectroscopy. The graph obtained is represented in FIG. 4.

Figure 4:
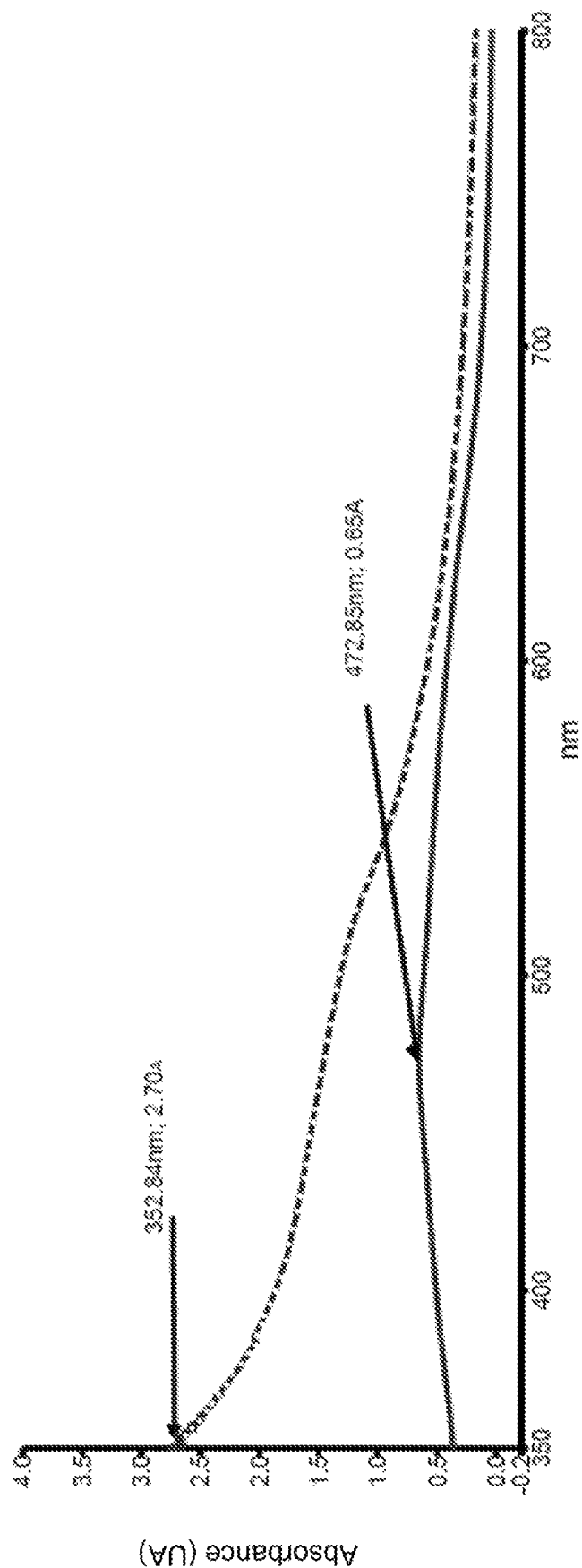
FIG. 4 shows the scanning graph of the extract, obtained from a sample extract according to Example 2 of the invention (■ ■ ■), as compared to the scanning graph of a conventional brown colouring agent (———) obtained between 350-800 nm by means of UV-Vis spectrophotometry.

In said FIG. 4, we may observe a single maximum corresponding to the reference colouring agent, Dark Brown CA, at 472.85 nm (———) and a maximum for the extract obtained according to Example 2 at 352.8 nm (■ ■ ■), 2.70 A, which is in the UV region.

Total Chromatogram of the Extract Obtained in Example 2

A new HPLC analysis of the extract obtained in Example 2 was performed, and said chromatogram was obtained within the 200-800 nm range.

In the total chromatogram of the extract, only one high-magnitude peak (1) was identified, with a spectrum similar to that obtained by means of UV-Vis (which represents the overall absorption of all the polyphenols present in the sample). See FIG. 5.

Using the spectrum of the compound with RT=33.2 (1), it was determined that one of the polyphenolic compounds present in the tannin extract isolated from grape seeds presents significant absorption within the visible range. This fact enhances the degree of fixation that said compound undergoes as compared to skins tanned with the tannin extract isolated from grape seeds obtained according to Example 2.

Light Fastness

In order to determine the light fastness of the extracts obtained according to the present invention, a comparative assay of the artificial light fastness according to the IUF 402 standard was performed. See FIG. 6, where 1 is leather tanned with Mimosa extract, 2 is leather tanned with Chestnut Tree extract, 3 is leather tanned with Quebracho Tree extract, 4 is leather tanned with Tara extract, 5 is leather tanned with grape seed extract using sodium metabisulfite (Example 1), 6 is leather tanned with grape seed extract using urea (Example 2).

The results of the assay confirm that the skin tanned with the extract isolated from grape seeds according to the invention, Examples 1 and 2, with and without a colouring agent, respectively, presents improved light stability. It is surprising that the presence of a colouring agent in the extract (see column 6) does not interfere with the light stability of the tanned skin even after 36 hours have elapsed (last row). Therefore, the light fastness of the tannin extract isolated from grape seeds according to the invention presents an improved light fastness as compared to the extracts in the prior art.

Determination of Certain Aromatic Amines Derived from Azo Colouring Agents (ISO 17234:2015) in Skin Tanned Using the Tannin Extract Isolated from Grape Seeds According to Example 2

Compliance with the ISO 17234-1:2015 standard (Second edition 2015 Apr. 1) to determine the presence of certain banned aromatic amines in azo colouring agents, which makes them suitable or not for general use, is well-known to persons skilled in the art.

This assay analyses the presence of certain analytes, i.e. certain aromatic amines, with a limit of detection of 30 mg/kg, in a tanned sample according to said ISO 17234-1:2015 standard. As a result of said analysis, the authors of the present invention confirm that the colouring agent is free of banned aromatic amines, which are listed in Table 5. Below we list the banned aromatic amines according to said ISO 17234-1:2015 standard in Table 5:

| BANNED AROMATIC AMINES | RESULTS |
| --- | --- |
| 4-aminobiphenyl (CAS No. 92-67-1) | Not detected[1] |
| benzidine (CAS No. 92-87-5) | Not detected[1] |
| 4-chloro-o-toluidine (CAS No. 95-69-2) | Not detected[1] |
| 2-naphthylamine (CAS No. 91-59-8) | Not detected[1] |
| o-amino-azotoluene (CAS No. 97-56-3) | Not detected[1] |
| 5-nitro-o-toluidine (CAS No. 99-55-8) | Not detected[1] |
| 4-chloroaniline (CAS No. 106-47-8) | Not detected[1] |
| 4-methoxy-m-phenylenediamine (CAS No. 615-05-4) | Not detected[1] |
| 4,4'-diaminophenylmethane (CAS No. 101-77-9) | Not detected[1] |
| 3,3'-dichlorobenzidine (CAS No. 91-94-1) | Not detected[1] |
| 3,3'-dimethoxybenzidine (CAS No. 119-90-4) | Not detected[1] |
| 3,3'-dimethylbenzidine (CAS No. 119-93-7) | Not detected[1] |
| 4,4'-methylene di-o-toluidine (CAS No. 838-88-0) | Not detected[1] |
| p-cresidine (CAS No. 120-71-8) | Not detected[1] |
| 4,4'-methylene-bis-(2-chloroaniline) (CAS No. 101-14-4) | Not detected[1] |
| 4,4'-oxydianiline (CAS No. 101-80-4) | Not detected[1] |
| 4-4'-thiodianiline (CAS No. 139-65-1) | Not detected[1] |
| o-toluidine (CAS No. 95-53-4) | Not detected[1] |
| 4-methyl-m-phenylenediamine (CAS No. 95-80-7) | Not detected[1] |
| 2,4,5-trimethylaniline (CAS No. 137-17-7) | Not detected[1] |
| o-anisidine (CAS No. 90-04-0) | Not detected[1] |
| 4-aminoazobenzene (CAS No. 60-09-3) | Not detected[1] |
| 2,4-xylidine (CAS No. 95-68-1) | Not detected[1] |
| 2,6-xylidine (CAS No. 27-62-7) | Not detected[1] |

[1]No banned aromatic amines were detected in the azo colouring agent.
Limit of detection <30 mg/kg.

Total Polyphenol Index (TPI)

The TPI, or total polyphenol index, is expressed as mg of gallic acid equivalents per gram of dry husk, is measured. This is a classic, robust spectrophotometric index for which the method described by Singleton et al. (Singleton, V. L.; Rossi, J. A., Jr., Colorimetry of total phenolics with phosphomolybdic-phosphotungstic acid reagents. Am. J. Enol. Vitic. 1965, 16, (3), 144-58) was used. 5 ml of the sample diluted in milli-Q water, 100 µl of the Folin-Ciocalteu reagent and 1 ml of a previously prepared 20 solution of sodium carbonate (20% $Na_2CO_3$ in Milli-Q $H_2O$) were introduced into a test tube. The mixture was vortex-agitated and allowed to rest at room temperature in the dark for 30 min, sufficient time for the Folin-Ciocalteu reagent to be reduced by the phenolic compounds under alkaline conditions, developing a blue colour. The spectrophotometric measurement was performed at 760 nm. Milli-Q water was used as the measurement blank. The total polyphenol concentration was calculated by means of a calibration curve for gallic acid ($y=0.0735x-0.0044$: $R^2=0.9985$), the concentration range whereof was (3-20 mg·l-125). The results were expressed as gallic acid equivalents (mg·l-1 GAE). The concentrations of the final extracts were expressed as mg of gallic acid per gram of dry husk (mg gallic acid/g dry weight).

Comparative data of the total polyphenol index provided by ES2443547 and the present invention are included below:

In ES2443547 (Example 1):
Total Polyphenol Index 18.31 mg GAE/g dry husk/1.83% (g GAE/100 g dry husk)
Gallic acid: 103 ppm (0.074 mg/g)/0.0074% (g GAE/100 g dry husk)
Catechin: 1692 ppm (1.21 mg/g)/0.121% (g GAE/100 g dry husk)
Epicatechin: 920 ppm (0.66 mg/g)/0.066% (g GAE/100 g dry husk)

The extract composition determined by means of the Folin-Ciocalteu method correspond to the 1.57%-2.43% interval of gallic acid.

Non information is provided regarding the type of polyphenolic compounds at the polymer level.

On the other hand, the polyphenolic extract is prepared using solvents different from water as the extraction media for the polyphenolic compounds.

The extraction yield according to the process disclosed by ES2443547 was 6.9% and the final extract only had obtained a total polyphenol content of 29% determined by means of High-Performance Liquid Chromatography (HPLC).

In the Present Invention (Example 1):
Total Polyphenol Index 8.23% of total polyphenols/dry seed or 82.31 mg GAE/g dry seed.
Gallic acid: 0.07 mg/g/0.0070% of gallic acid over dry seed;
(−)-Epicatechin: 0.027 mg/g dry seed/0.0027% over dry seed;

No presence of catechin is detected in the chromatogram of the sample Example 1. The total polyphenol content determined by means of High-Performance Liquid Chromatography (HPLC-DAD) is as high as, and higher than, 50% in a one-pot extraction, and in a single aqueous extraction step.

Characteristics of the Grape Seed Extract Obtained

The nature of the tannins is a mixture of the pure condensed type (catechinic) and the pure hydrolysable type (pyrogallic);

The extract comprises non-tannins that include gallic acid; their presence is believed to be responsible for a better antioxidant action and a better light fastness.

The extract is soluble in a cold aqueous medium;

It has applications as a tanning agent for hides and skins;

It has applications as an antioxidant agent in food, cosmetics and pharmaceutical products;

It has applications as a colouring agent in tanning, food, cosmetics and pharmaceutical products;

It presents improved light fastness, between the extract from Chestnut Tree 2 and the extract from Tara 4;

The colour of the tanned product is similar to that obtained with the Chestnut Tree extract.

Although we have referred to a specific embodiment of the invention, it is evident to persons skilled in the art that the process described is susceptible to numerous variations and modifications, and that all the details mentioned above may be replaced with other technically equivalent ones, without going beyond the scope of protection defined by the attached claims.

The invention claimed is:

1. A tannin extract obtained by a method comprising:
(a) adding an aqueous solution of a polyphenol-solubilizing agent to whole grape seeds without grinding or milling, wherein the polyphenol-solubilizing agent is selected from the group consisting of urea, sodium hydroxide, and a compound containing an $SO_3$ group and is present at a concentration in the aqueous solution of 1-15% by weight with respect to the weight of the whole grape seeds;
(b) reacting the aqueous solution of the polyphenol-solubilizing agent and the whole grape seeds at a pressure ranging between 2.5 and 3.5 atmospheres, and a temperature ranging between 100° C. and 160° C., in a period of time ranging from 1-2 hours in an autoclave reactor; and
(c) recovering a liquid extract from the autoclave reactor, wherein the liquid extract comprises a mixture of pure hydrolysable tannins, pure condensed tannins that include procyanidins, and non-tannins that include gallic acid, and further wherein the liquid extract has a content of tannins or polyphenols that is greater than 50%.

2. A device comprising the tannin extract of claim 1.

3. The device of claim 2, wherein the device comprises leather.

4. The device of claim 2, wherein the device is a food.

5. The device of claim 2, wherein the device is a cosmetic.

6. The device of claim 2, wherein the device is a drug.

7. A method of producing an aqueous liquid tannin extract comprising:
(a) adding an aqueous solution of a polyphenol-solubilizing agent to whole grape seeds without grinding or milling, wherein the polyphenol-solubilizing agent is selected from the group consisting of urea, sodium hydroxide, and a compound containing an SO3 group and is present at a concentration in the aqueous solution of 1-15% by weight with respect to the weight of the whole grape seeds;
(b) reacting the aqueous solution of the polyphenol-solubilizing agent and the whole grape seeds at a pressure ranging between 2.5 and 3.5 atmospheres, and a temperature ranging between 100° C. and 160° C., in a period of time ranging from 1-2 hours in an autoclave reactor; and
(c) recovering a liquid extract from the autoclave reactor, wherein the liquid extract comprises a mixture of pure hydrolysable tannins, pure condensed tannins that include procyanidins, and non-tannins that include gallic acid, and further wherein the liquid extract has a content of tannins or polyphenols that is greater than 50%.

8. The process according to claim 7, wherein the polyphenol-solubilising agent is urea whereby further extracting in the tannin extract an azo colouring agent free of banned aromatic amines showing a maximum at 352.8 nm, 2.70 A, measured by UV-Vis spectroscopy between 350-800 nm.

9. The process according to claim 7, wherein the concentration of the polyphenol-solubilising agent in the aqueous solution ranges between 2% and 8% by weight with respect to the weight of the whole grape seeds.

10. The process according to claim 7, wherein the weight ratio between the grape seeds and the water used to prepare the aqueous solution ranges between 0.5:1 and 1:4.

11. The process according to claim 7, wherein the extraction step is performed at a temperature ranging between 100° C. and 130° C., and a pressure ranging between 2.5 and 3.5 atmospheres.

12. The process according to claim 7, wherein, once the extraction process has been completed, the reactor is cleaned with new water that is susceptible to being reused to prepare a new aqueous solution of the polyphenol-solubilising agent.

13. The tannin extract according to claim 1, wherein the polyphenol-solubilizing agent is urea and the tannin extract further comprises an azo coloring agent free of banned aromatic amines and shows a maximum at 352.8 nm, 2.70 A, measured by UV-Vis spectroscopy between 350-800 nm.

14. The process of claim 7, further comprising concentrating the extract by evaporation, to obtain the isolated tannin extract in a concentrated form.

15. The process of claim 7, further comprising spray drying, to obtain the isolated tannin extract in the solid state.

* * * * *